United States Patent
Deshpande

(10) Patent No.: US 6,555,287 B1
(45) Date of Patent: Apr. 29, 2003

(54) NON-SUBLIMING, DIFUNCTIONALIZED ULTRAVIOLET DYES FOR USE IN ANTI-REFLECTIVE COATINGS

(75) Inventor: Shreeram V. Deshpande, Rolla, MO (US)

(73) Assignee: Brewer Science, Inc., Rolla, MO (US)

( * ) Notice: Subject to any disclaimer, the term of this patent is extended or adjusted under 35 U.S.C. 154(b) by 79 days.

(21) Appl. No.: 09/684,999

(22) Filed: Oct. 10, 2000

(51) Int. Cl.⁷ .................. G03F 7/004; G03C 1/492; C07C 69/76; C07C 255/00
(52) U.S. Cl. ................ 430/270.1; 430/271.1; 560/53; 560/55; 560/81; 560/82; 562/489; 564/347; 558/401; 549/543; 568/631; 568/715
(58) Field of Search .................. 430/270.1, 271.1; 562/489; 560/53, 55, 81, 82; 568/631, 715; 564/347; 558/401; 549/543

(56) References Cited

U.S. PATENT DOCUMENTS 4,544,691 A    10/1985    Dexter et al.
4,806,604 A  * 2/1989    Tsien et al. ............... 549/439
5,688,987 A    11/1997    Meador et al.

OTHER PUBLICATIONS

CAplus 111:246747 to Potvin et al, 1989.*

* cited by examiner

Primary Examiner—Rosemary Ashton
(74) Attorney, Agent, or Firm—Hovey Williams LLP

(57) ABSTRACT

An improved light attenuating compound for use in the production of microdevices is provided. Broadly, the light attenuating compound is difunctional and can be directly incorporated (either physically or chemically) into photolithographic compositions such as anti-reflective coatings (ARC) and contact or via hole fill materials. The preferred light attenuating compound comprises functional groups electronically isolated from the light absorbing moieties of the compound. As a result, the spectral properties of the compound are not negatively affected when the functional groups form bonds with other compounds during polymerization or crosslinking.

21 Claims, No Drawings

NON-SUBLIMING, DIFUNCTIONALIZED ULTRAVIOLET DYES FOR USE IN ANTI-REFLECTIVE COATINGS

BACKGROUND OF THE INVENTION

1. Field of the Invention

The present invention is broadly concerned with new dyes or light attenuating compounds for incorporation into photolithographic compositions (e.g., anti-reflective coatings and contact or via hole fill compositions) utilized in the manufacturing of microdevices. More particularly, the light attenuating compounds comprise at least two reactive functional groups and are especially useful for absorbing light at wavelengths of from about 180–450 nm. Through these functional groups, the compounds can chemically bond with a polymer binder already present in the composition or can be polymerized with a precursor polymer to form a polymer binder for use in the composition without negatively affecting the spectral properties of the light attenuating compound.

2. Description of the Prior Art

Anti-reflective coatings (ARC) have long been used in semiconductor manufacturing to control standing waves and critical dimensions (CD) of the patterned photoresists used in microlithography. As the feature size on semiconductor devices continue to decrease, CD control becomes very critical.

Currently available compositions for use as ARC's in submicron microlithography typically comprise an organic polymer binder and an ultraviolet dye that is attached to the polymer binder by a functional group on the dye. This functional group is usually part of a conjugated, electronic structure that is responsible for the light absorbing properties of the dye. However, since reactions of the functional group alter the electronic structure of the dye, undesirable spectral shifts generally result when the dye is attached to the binder. Furthermore, a reduction in the light absorbing abilities of the dye may also occur if the functional group degrades (e.g., oxidizes) during the attachment reaction. Similar problems occur when the dye is incorporated into the polymer binder in a linear fashion using two-point attachment via two functional groups on the dye.

Thus, there is a need for a dye which can be attached to or polymerized with a polymer binder for incorporation into an ARC with minimal impact on the light absorbing abilities of the dye.

SUMMARY OF THE INVENTION

The present invention overcomes these problems by broadly providing a dye or light attenuating compound which can be incorporated into ARC's without negatively affecting the dye's light-absorbing abilities.

In more detail, the inventive dye has the structure of Formula I or Formula II.

Formula I

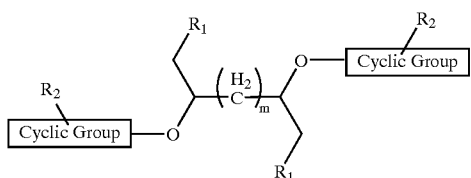

Formula II

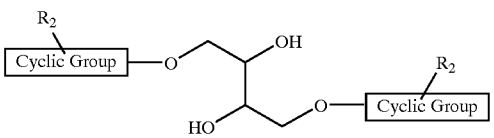

wherein:

each cyclic group can be the same or different groups and is preferably individually selected from the group consisting of aromatic groups (with benzene rings being the most preferred aromatic group);

m=0–30, preferably 0–15, and more preferably 0–6;

each $R_1$ is individually a reactive group such as those selected from the group consisting of —OH, —COOH, —NH$_2$, —COOR' (with R' being an alkyl group (preferably $C_1$–$C_8$)), —CH=CH$_2$, and epoxy groups;

preferably all but one ring member of the cyclic group has an $R_2$ bonded thereto, and each $R_2$ is individually selected from the group consisting of hydrogen, alkyls, heteroalkyls, aryls, heteroaryls, ethers, thioethers, carboxylates, cyanos, halogens, R"—C=N—, R"—N=N' (with R" being hydrogen or an alkyl group (preferably $C_1$–$C_8$)), dialkylaminos, diarylaminos, and one of the following:

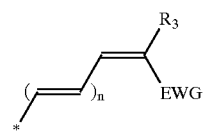

or

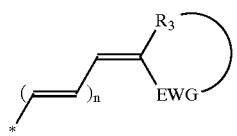

where n=0 or 1 in structure A, where EWG and $R_3$ do not form a cyclic unit:

EWG is an electron-withdrawing group such as those selected from the group consisting of carbonyls, cyanos, iminos, carboxylic acids, carboxylic esters, carboxamidos, carboximidos, and sulfonyls; and $R_3$ is selected from the group consisting of hydrogen, alkyls, heteroalkyls, aryls, heteroaryls, carbonyls, cyanos, iminos, carboxylic acids, carboxylic esters, carboxamidos, carboximidos, and sulfonyls; and in structure B, EWG and $R_3$ form a cyclic electron-withdrawing unit which includes one or more groups selected from the group consisting of carbonyls, cyanos, iminos, carboxylic acids, carboxylic esters, carboxamidos, carboximidos, and sulfonyls, and in either Structure A or B, (*) indicates the point of attachment of $R_2$ to the cyclic group.

Even more preferably, the dye has the structure depicted in Formula III.

Formula III

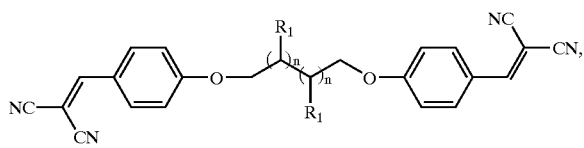

wherein each n=1–30, and preferably 1–10, and each $R_1$ is individually a reactive group such as those selected from the group consisting of —OH, —COOH, —NH$_2$, —COOR" (with R' being an alkyl group (preferably $C_1$–$C_8$)), —CH=CH$_2$, and epoxy groups, with —OH groups being particularly preferred.

Examples of particularly preferred Structures B where EWG and $R_3$ form a cyclic electron-withdrawing unit include the structure depicted in Formula IV.

Formula IV

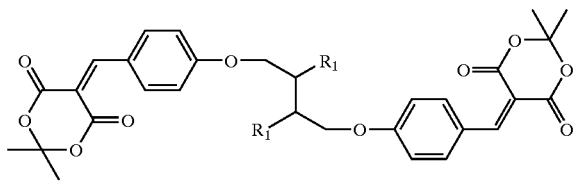

wherein each $R_1$ is individually a reactive group such as those selected from the group consisting of —OH, —COOH, —NH$_2$, —COOR' (with R' being an alkyl group (preferably $C_1$–$C_8$)), —CH=CH$_2$, and epoxy groups.

In each of the foregoing dye structures, the reactive functionalities (i.e., the $R_1$ groups) are electronically isolated from the light-absorbing portion (i.e., the cyclic group) of the structure so that spectral shifts and degradation are minimized or avoided when the dye is polymerized, crosslinked, or otherwise reacted. Additionally, it will be appreciated that the $R_1$ groups can be selected to react with, for example, aminoplast, polyepoxide, polyisocyanate, or polycarboxylic acid crosslinking agents, thus allowing for the design of a wider variety of polymer classes for incorporation into ARC's for use at wavelengths of about 180–450 nm.

In the embodiment illustrated in Formula IV, the dye comprises a blocked functionality on its light absorbing moiety which allows for selective dissolution in organic solvents or aqueous media. For example, the structure of Formula IV will hydrolyze in the presence of photogenerated acids (such as acids formed in photoresist layers upon exposure of the layer to ultraviolet light) to form a base-soluble carboxylic acid. Thus, because the developer is typically a base, the resulting ARC will be etchable and subsequent plasma etching will not be necessary.

The inventive dyes can be physically mixed with a polymer binder and crosslinking agent and dissolved in a solvent system to form a composition useful for forming an ARC which can absorb at a defined wavelength or can exhibit broadband absorption (e.g., at 193, 248, and 365 nm). However, it is particularly preferred that the dye be bonded to the polymer binder. In the latter instance, the dye can be bonded to a functional group on the polymer binder or it can be polymerized with precursor polymers (preferably by step-wise methods to form linear polymers) without interfering with the spectral properties of the dye. That is, the absorbance at a wavelength of from about 180–450 nm of an ARC comprising an inventive dye bonded to or polymerized with a polymer binder is at least about 25%, preferably at least about 35%, and more preferably at least about 50% of the absorbance of the dye alone (i.e., of the dye when it is not bonded to or polymerized with another compound).

In applications where the dye is polymerized with a precursor polymer, the polymerization reaction preferably results in bonds being formed between the precursor polymer and the $R_1$ groups on the dye structure. The resulting polymer can be incorporated into an anti-reflective composition and should have a weight average molecular weight of from about 20,000–100,000 Daltons.

Preferred precursor polymers include those selected from the group consisting of polyesters, polyacrylates, polyheterocyclics, polyetherketones, polyisocyanates, polyhydroxystyrene, polycarbonates, polyepichlorohydrin, polyvinyl alcohol, oligomeric resins, and mixtures thereof. Suitable solvent systems comprise solvents selected from the group consisting of ethylene glycol monomethyl ether acetate, propylene glycol monomethyl ether acetate, ethyl lactate, N-methylpyrrolidone, gamma-butyrolactone, tetrahydrofurfuryl alcohol, cyclohexanone, butyl acetate, diglyme, and diacetone alcohol.

The anti-reflective composition can be applied to the surface of a substrate (e.g., silicon wafer) according to conventional methods (e.g., spin-coating) to form an anti-reflective layer. The layer can then be baked, preferably at a temperature of at least about 160° C., after which a photoresist layer can be applied to the anti-reflective layer. The photoresist layer can then be exposed to light at the desired wavelength followed by developing of the layer and subsequent etching of the developed layer according to known processes.

Advantageously, anti-reflective layers formed according to the invention have superior spectral properties. For example, at wavelengths of from about 180–450 nm, the anti-reflective layers have a molar extinction coefficient of at least about 10,000 L/mol-cm. The anti-reflective layer also has a k value of at least about 0.25, and preferably at least about 0.30 at a wavelength of about 365 nm. Finally, anti-reflective layers formed according to the invention are essentially non-subliming at temperatures of at least about 100° C., preferably at least about 150° C., and more preferably from about 160–220° C. after baking on a hotplate under conventional conditions (e.g., baking at about 160° C. for about 30 seconds).

When used in reference to Formulas I–IV, the term "compound" is intended to refer to the actual compound represented in the particular Formula, as well as all functional moieties thereof. Thus, "compound of Formula I" also refers to, for example, moieties of Formula I which are bonded to a polymer binder in an anti-reflective coating composition.

DETAILED DESCRIPTION OF THE PREFERRED EMBODIMENTS

EXAMPLES

The following example sets forth preferred methods in accordance with the invention. It is to be understood, however, that these examples are provided by way of illustration and nothing therein should be taken as a limitation upon the overall scope of the invention.

A generic reactin scheme by which the inventive dye structures can be formed is depicted in Scheme A.

Scheme A

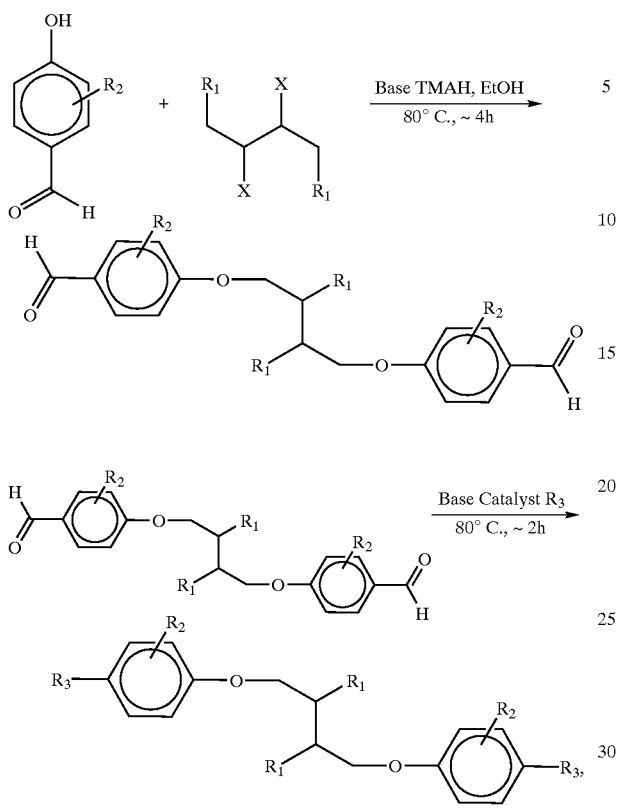

Scheme B

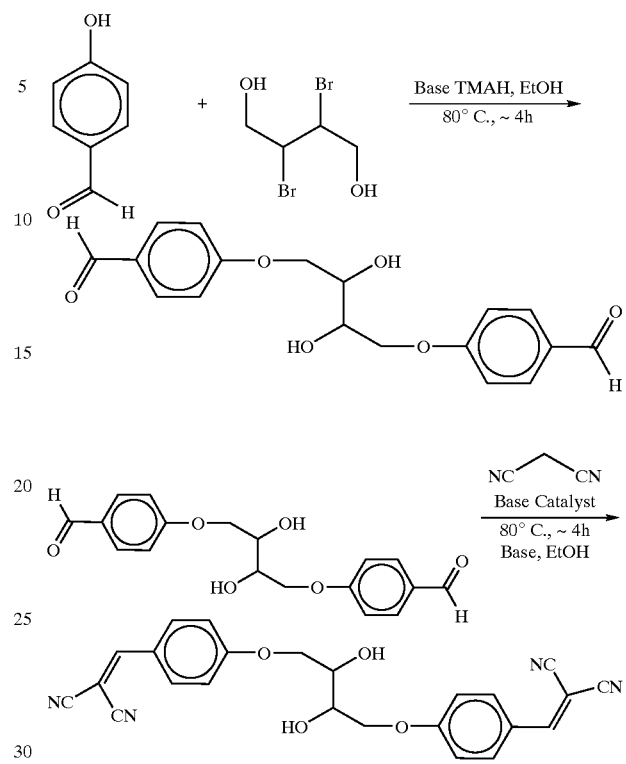

wherein: $R_1$ and $R_2$, are as discussed above with respect to Formulas I and II; $R_3$ is an electron-withdrawing group such as those selected from the group consisting of carbonyls, cyanos, iminos, carboxycylic esters, carboximides, carboximidos, and sulfonyls, or a masked, crosslinking group such as those selected from the group consisting of —COOH, —OH, and —NH$_2$; and X is selected from the group consisting of the halogens and —OR (where R is preferably a $C_1$–$C_{20}$ alkyl group), $N_2$, and alkyl carbonates.

Example 1

The reaction scheme for this test is set forth in Scheme B. A three-necked, round-bottomed flask fitted with a reflux condensor and an $N_2$ inlet. A magnetic stirrer was charged with 20.0 g (0.16 mol, 2 eq.) of 4-hydroxybenzaldehyde (1) and 20.32 g (0.082 mol, 1 eq.) of 2,3-dibromo-, 1,4-butanediol (2) in the presence of 25% (aq) tetramethylammonium hydroxide (TMAH) (1:1 mol ratio with 4-hydroxybenzaldehyde) in refluxing ethanol for approximately 4 hours. The intermediate dialdehyde, 1,4-(4-hydroxy-benzaldehyde)-2,3-butanediol (3), precipitated out upon cooling of the reaction mixture to room temperature and adding of water to the reaction mixture. The dialdehyde was filtered under vacuum and dried in a vacuum oven overnight. The dialdehyde was obtained in a reasonable yield (65%–85%) and then converted into a dye (which absorbed light at 365 nm) by reacting 3.0 g (0.009 mols, 1 eq.) of the dialdehyde with 1.18 g (0.018 mols, 2 eq.) of malononitrile (4) using triethylamine as the catalyst in refluxing ethanol. The reaction was carried out by refluxing the reaction mixture for about 2 hours in a three-necked flask fitted with an $N_2$ inlet, reflux condensor, and magnetic stirrer. As soon as the reaction started, bis-1,4-(1,4 dicyanovinyl)-2,3-butanediol (5) began precipitating out of the reaction mixture. The resulting yellow dye was then filtered, dried in a vacuum oven, and used to formulate an ARC.

I claim:

1. In a curable composition for use during microlithographic processes, said composition comprising a polymer binder dissolved in a solvent system, the improvement which comprises: a light attenuating compound selected from the group consisting of

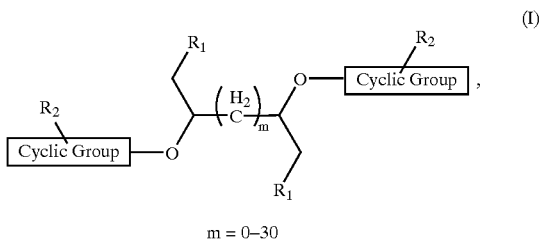

m = 0–30

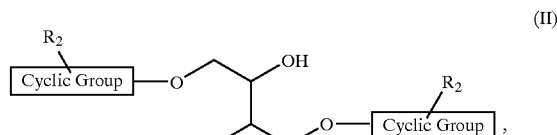

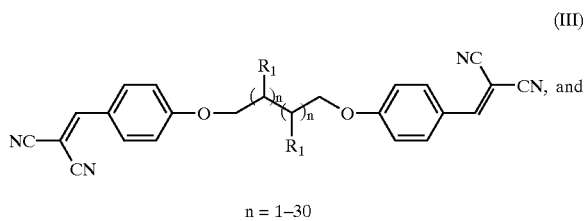

n = 1–30

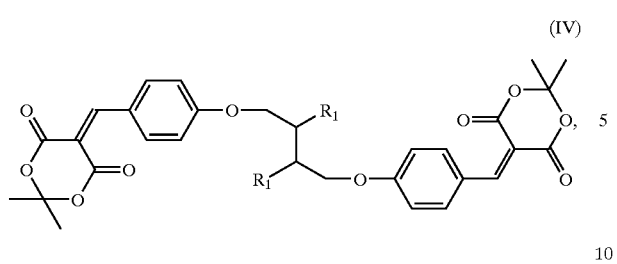

(IV)

wherein:
  each cyclic group is an aromatic group;
  each $R_1$ is individually selected from the group consisting of —OH, —COOH, —NH$_2$, —COOR', —CH=CH$_2$, and epoxy groups, where R' is an alkyl group; and
  each $R_2$ is individually selected from the group consisting of hydrogen, alkyls, heteroalkyls, aryls, heteroaryls, ethers, thioethers, carboxylates, cyanos, halogens, R"—C=N—, R"—N=N',
  where R" is hydrogen or an alkyl group, dialkylaminos, diarylaminos, and one of the following:

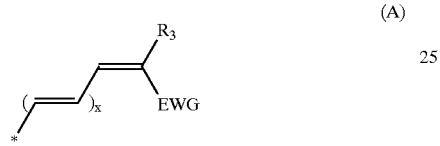

(A)

or

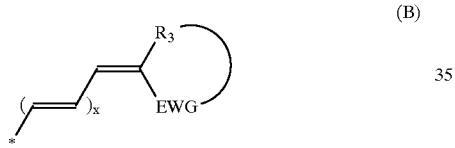

(B)

x=0 or 1,
wherein, * indicates the point of attachment of $R_2$ to the cyclic group, and in Structure A:
  EWG is selected from the group consisting of carbonyls, cyanos, iminos, carboxylic acids, carboxylic esters, carboxamidos, carboximidos, and sulfonyls; and
  $R_3$ is selected from the group consisting of hydrogen, alkyls, heteroalkyls, aryls, heteroaryls, carbonyls, cyanos, iminos, carboxylic acids, carboxylic esters, carboxamidos, carboximidos, and sulfonyls; and
wherein, in structure B, EWG and $R_3$ are selected from the group consisting of carbonyls, cyanos, iminos, carboxylic acids, carboxylic esters, carboxamidos, carboximidos, and sulfonyls.

2. The composition of claim 1, wherein each $R_1$ comprises an —OH group.

3. The composition of claim 1, wherein each $R_2$ group individually has a structure according to (B).

4. The composition of claim 1, wherein said solvent system comprises a solvent selected from the group consisting of ethylene glycol monomethyl ether acetate, propylene glycol monomethyl ether acetate, ethyl lactate, N-methylpyrrolidone, gamma-butyrolactone, tetrahydrofurfuryl alcohol, cyclohexanone, butyl acetate, diglyme, and diacetone alcohol.

5. The composition of claim 1, wherein said polymer binder comprises a polymer selected from the group consisting of polyesters, polyacrylates, polyisocyanates, polyheterocyclics, polyetherketones, polyhydroxystyrene, polycarbonates, polyepichlorohydrin, polyvinyl alcohol, oligomeric resins, and mixtures thereof.

6. A light attenuating compound having the formula:

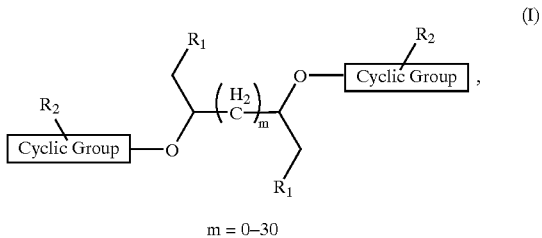

(I)

m = 0–30 wherein:
  each cyclic group is an aromatic group,
  each $R_1$ is individually selected from the group consisting of —OH, —COOH, —NH$_2$, —COOR', —CH=CH$_2$, and epoxy groups, where R' is an alkyl group;
  each $R_2$ is individually selected from the group consisting of hydrogen, alkyls, heteroalkyls, aryls, heteroaryls, ethers, thioethers, carboxylates, cyanos, halogens, R"—C=N—, R"—N=N', where R" is hydrogen or an alkyl group, dialkylaminos, diarylaminos, and one of the following:

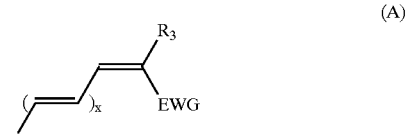

(A)

or

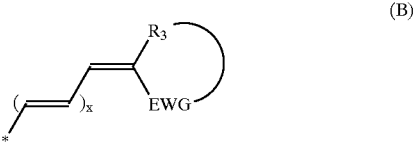

(B)

x=0 or 1,
wherein, * indicates the point of attachment of $R_2$ to the cyclic group, and in Structure A:
  EWG is selected from the group consisting of carbonyls, cyanos, iminos, carboxylic acids, carboxylic esters, carboxamidos, carboximidos, and sulfonyls; and
  $R_3$ is selected from the group consisting of hydrogen, alkyls, heteroalkyls, aryls, heteroaryls, carbonyls, cyanos, iminos, carboxylic acids, carboxylic esters, carboxamidos, carboximidos, and sulfonyls, and
wherein, in structure B, EWG and $R_3$ are selected from the group consisting of carbonyls, cyanos, iminos, carboxylic acids, carboxylic esters, carboxamidos, carboximidos, and sulfonyls.

7. The compound of claim 6, wherein each $R_1$ comprises an —OH group.

8. The compound of claim 6, wherein each $R_2$ group individually comprises a structure according to (B).

9. The combination of a substrate having a surface and an anti-reflective layer on said substrate surface, said anti-reflective layer including therein a light attenuating compound selected from the group consisting of:

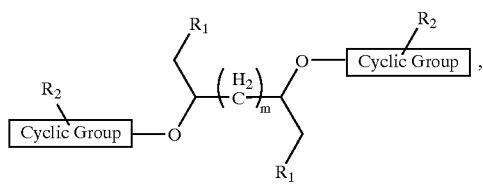

(I)

m = 0–30

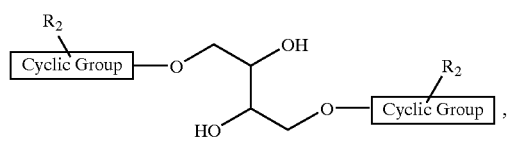

(II)

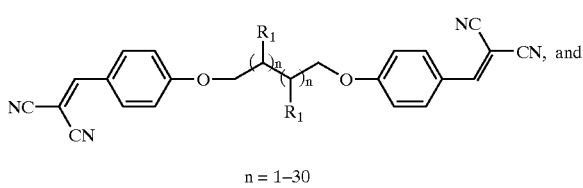

(III)

n = 1–30

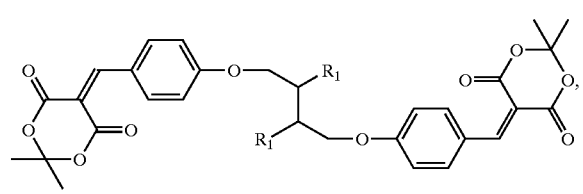

(IV)

wherein:

each cyclic group is an aromatic group;

each $R_1$ is individually selected from the group consisting of —OH, —COOH, —NH$_2$, —COOR', —CH=CH$_2$, and epoxy groups, where R' is an alkyl group; and each $R_2$ is individually selected from the group consisting of hydrogen, alkyls, heteroalkyls, aryls, heteroaryls, ethers, thioethers, carboxylates, cyanos, halogens, R"—C=N—, R"—N=N', where R" is hydrogen or an alkyl group, dialkylaminos, diarylaminos, and one of the following:

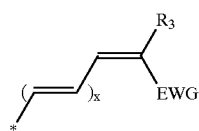

(A)

or

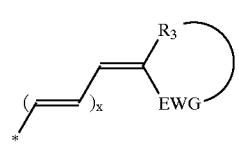

(B)

x=0 or 1, wherein, * indicates the point of attachment of $R_2$ to the cyclic group, and in Structure A:

EWG is selected from the group consisting of carbonyls, cyanos, iminos, carboxylic acids, carboxylic esters, carboxamidos, carboximidos, and sulfonyls; and $R_3$ is selected from the group consisting of hydrogen, alkyls, heteroalkyls, aryls, heteroaryls, carbonyls, cyanos, iminos, carboxylic acids, carboxylic esters, carboxamidos, carboximidos, and sulfonyls; and wherein, in structure B, EWG and $R_3$ are selected from the group consisting of carbonyls, cyanos, iminos, carboxylic acids, carboxylic esters, carboxamidos, carboximidos, and sulfonyls.

10. The combination of claim 9, wherein each $R_1$ comprises an —OH group.

11. The combination of claim 9, wherein each $R_2$ group individually comprises a structure according to (B).

12. The combination of claim 9, wherein said anti-reflective layer has a k value of at least 0.25 at about 365 nm.

13. The combination of claim 9, wherein said anti-reflective layer is baked and is essentially non-subliming at temperatures of at least about 100° C.

14. A method of forming a precursor structure for use in manufacturing integrated circuits, said method comprising the step of applying a quantity of an anti-reflective composition according to claim 1 to the surface of a substrate to form an anti-reflective layer on said substrate surface.

15. The method of claim 14, wherein said anti-reflective layer has a k value of at least about 0.25 at about 365 nm.

16. The method of claim 14, further including the step of baking said anti-reflective layer at a temperature of at least about 160° C. after said applying step.

17. The method of claim 16, further including the step of applying a photoresist layer to said baked anti-reflective layer.

18. The method of claim 17, further including the steps of:

exposing at least a portion of said photoresist layer to activating radiation;

developing said exposed photoresist layer; and etching said developed photoresist layer.

19. The method of claim 18, wherein said anti-reflective layer is essentially non-subliming at temperatures of at least about 100° C.

20. A light attenuating compound having a formula selected from the group consisting of:

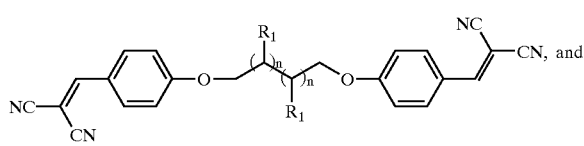

(III)

n = 1–30 n=1–30(III), and
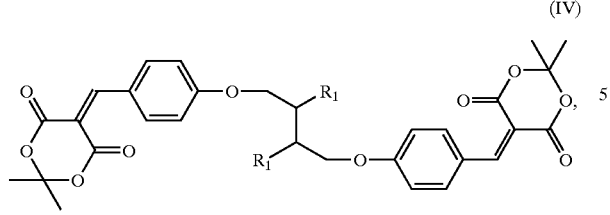
(IV),
wherein $R_1$ is selected from the group consisting of —OH, —COOH, —NH$_2$, —COOR', —CH=CH$_2$, and epoxy groups, where R' is an alkyl group.
21. The compound of claim 20, wherein each $R_1$ comprises an —OH group.
* * * * *